United States Patent
Wolf et al.

(10) Patent No.: US 7,065,450 B2
(45) Date of Patent: Jun. 20, 2006

(54) PROCESS FOR PRODUCTION OF NEW CATALYSTS USING AN EVOLUTIONARY PROCESS

(75) Inventors: Dorit Wolf, Oberursel (DE); Manfred Baerns, Berlin (DE); Olga Gerlach, Ludwigshafen (DE)

(73) Assignee: Institut fur Angewandte Chemie Berlin-Adlershof e.V. (DE)

( * ) Notice: Subject to any disclaimer, the term of this patent is extended or adjusted under 35 U.S.C. 154(b) by 214 days.

(21) Appl. No.: 09/909,038

(22) Filed: Jul. 19, 2001

(65) Prior Publication Data

US 2002/0076726 A1    Jun. 20, 2002

(30) Foreign Application Priority Data

Jul. 20, 2000   (DE) ................ 100 37 166

(51) Int. Cl.
*G01N 33/48* (2006.01)
*B01J 35/08* (2006.01)
*B01J 31/00* (2006.01)
*B01J 23/00* (2006.01)

(52) U.S. Cl. ............... 702/19; 702/20; 502/9; 502/111; 502/123; 502/300

(58) Field of Classification Search ............ 702/19, 702/20; 502/9, 300, 111, 123
See application file for complete search history.

(56) References Cited

FOREIGN PATENT DOCUMENTS

| WO | WO 00/15341 | 3/2000 |
|---|---|---|
| WO | WO 00/40331 | 7/2000 |

OTHER PUBLICATIONS

Hanes, et al., "In vitro selection methods for screening of peptide and protein libraries", CAPLUS, 1999:570827.

*Primary Examiner*—John Brusca
*Assistant Examiner*—Shubo (Joe) Zhou
(74) *Attorney, Agent, or Firm*—Akerman Senterfitt; Stephan A. Pendorf

(57) ABSTRACT

This invention relates to a process wherein improved production of catalysts is made possible according to an evolutionary method. The principles of mutation and crossing of catalyst components and determination of performance parameters of the mixed catalysts used here are carried out in 5 to 50 catalyst generations in such way that two mixed catalysts are selected from the same generation in crossing, and at least one selected component is exchanged between the two, and in mutation of a selected mixed catalyst, a selected component from a catalyst mixture is introduced into the catalyst or, if already present in it, it is removed from the catalyst. The selection is made in all cases by using random generators with a uniform distribution. The same procedure is used for the gas flow composition, the temperature and the space velocity as the other performance parameters.

8 Claims, 2 Drawing Sheets

|  | Precursor generation | | Subsequent generation | |
|---|---|---|---|---|
|  | A | B | A | B |
| V | 0 | 1 | 0 | 1 |
| Mg | 1 | 0 | 1 | 0 |
| Crossing point → B | 0 | 1 | 1 | 0 |
| Mo | 1 | 0 | 1 | 0 |
| La | 0 | 0 | 0 | 0 |
| Mn | 0 | 0 | 0 | 0 |
| Fe | 1 | 0 | 1 | 0 |
| Ga | 0 | 0 | 0 | 0 |

Diagram of crossing

|  | Precursor generation | Subsequent generation |
|---|---|---|
| V | 1 | 1 |
| Mg | 0 | 0 |
| B | 1 | 1 |
| Mo | 1 | 1 |
| La | 1 | 1 |
| Mn | 1 | 0 |
| Fe | 1 | 1 |
| Ga | 0 | 0 |

Diagram of mutation

Figure 2

PROCESS FOR PRODUCTION OF NEW CATALYSTS USING AN EVOLUTIONARY PROCESS

BACKGROUND OF THE INVENTION

1. Field of the Invention

This invention relates to a process which permits an improved production and selection of catalysts according to an evolutionary process.

2. Description of the Related Art

The art describes a method of producing active and or selective catalysts from inorganic and organometallic solids or mixtures thereof, whereby potentially catalytic active individual components are first identified in the evolutionary search and optimization method, and by their randomized qualitative and quantitative combination with numerous materials, a first generation of mixed materials is produced and then subjected to catalytic testing. In addition, it has already been reported that to produce a new generation according to the principles of mutations and crossing, the best materials of the first generation are selected. This procedure has then been used further for all subsequent generations. However, it has been found that although this procedure leads to catalysts containing catalytically active components, other original components are already removed from the remaining selection process in the first or subsequent generations despite the fact that they could be necessary for an optimum catalyst.

SUMMARY OF THE INVENTION

The object of this invention is to further improve upon the evolutionary selection strategy and to include catalyst components and performance parameters.

According to this invention, the range of available catalyst components in evolutionary selection, where choices are narrowed down, is kept broader so that in progressing from the first "randomized" step to the following generations created on the basis of an evolutionary selection strategy, some of the original components are not lost after one or a few successive generations. This method thus leads to a greater targeting accuracy in the selection process.

This requires a stronger representation of mixed materials having a good catalytic efficiency in the following generations but at the same time retaining at first the mixed materials that are not excellent but whose individual components might be quite beneficial in other combinations, in order to thereby review their possibly positive effect in the following generations. Only when it is found in the evolutionary optimization process that these individual components do not contribute to an improvement in the catalytic materials are they ruled out during the further evolutionary process.

Instead of individual components, in the case of an intended improvement in the catalyst, already known catalyst compositions may also be introduced as pseudo-components into the first and subsequent generations.

Therefore, according to this invention, the process for producing active heterogeneous catalysts of an inorganic nature through selection of solid materials having various compositions and through restructuring of the original catalysts and subsequent catalyst generations by means of stochastic methods and determination of the performance parameters of the respective catalyst generation and selection of the mixed catalysts of one or more catalyst generations is characterized in that the restructuring, if based on the principle of crossing, takes place in such a way that a mixed catalyst is randomly selected from a generation of catalysts by means of a numerical random generator with a uniform distribution (e.g., by means of the program code GO5DYF of the NAG LIBRARY [NAG FORTRAN WORKSTATION LIBRARY, NAG Group Ltd., 1986]), and a second mixed catalyst is selected from the same generation with the probability W by means of numerical random generators with a uniform distribution (for example, by means of a combination of the program codes GO5DYF and GO5DZF of the NAG LIBRARY [NAG FORTRAN WORKSTATION LIBRARY, NAG Group Ltd., 1986]), where the following formulation is selected by $W_i$ $$W_i = \frac{\left(\sum_{j=1}^{n} j\right) - i}{\left(\sum_{j=1}^{n} j\right)}$$

where i and j denote the ranking of the catalysts of one generation, ranked according to decreasing catalytic activity, and n is the number of catalysts in one generation, and then from the two mixed catalysts to be crossed, at least one individual component which is present in only one of the two catalysts is selected according to the random principle by means of a numerical random generator with a uniform distribution (for example, by means of the program code GO5DYF of the NAG LIBRARY [NAG FORTRAN WORKSTATION LIBRARY, NAG Group Ltd., 1986]) and two new catalyst compositions of the next generation are defined in such a way that the selected component is then added to the catalyst which did not contain this component in the preceding generation, while the component in the catalyst containing it originally is omitted, and the restructuring of a catalyst of the next generation, when it is based on the principle of mutation, takes places in such a manner that first a mixed catalyst is randomly selected from a catalyst generation by means of a numerical random generator with a uniform distribution (for example, by means of the program code GO5DYF of the NAG LIBRARY [NAG FORTRAN WORKSTATION LIBRARY, NAG Group Ltd., 1986]), and then a single component is selected according to the random principle by means of a numerical random generator with a uniform distribution (for example, by means of the program code GO5DYF of the NAG LIBRARY [NAG FORTRAN WORKSTATION LIBRARY, NAG Group Ltd., 1986]), and if this individual component is already contained in the mixed catalyst, it is removed or, if it has not yet been contained in this catalyst, it is added to it.

This type of crossing and mutation is carried out until the mixed catalysts produced in this way no longer show any definite improvement within one generation. In this way it is possible to allow individual components to participate in the process of selection and testing of the properties of the newly structured mixed materials for a longer period of time and to cull them out only when no further improvement in properties with respect to catalytic activity and/or selectivity is clearly discernible any longer in the corresponding mixed catalysts.

All the chemical elements and support components for catalysts which are also listed in German Patent Application 19843242.9 and International Patent 00/15341, to which reference is herewith made explicitly, may be used as catalytic components, i.e., Li, Na, K, Mg, Ca, Sr, Ba, Y, La, Ti, Zr, V, Nb, Cr, Mn, Tc, Re, Fe, Ru, Os, Co, Rh, Ir, Ni, Pd, Pt, Cu, Ag, Au, Zn, Cd, Hg, B, Al, Ga, In, C, Si, Sn, Pb, N, P, As, Sb, Bi, S, Se, Te, F, Cl, Ce, Nd, or as catalytic supports, the oxides, carbonates, carbides, nitrides, borides of Mg, Ca, Sr, Ba, La, Zr, Ce, Al, Si or mixtures thereof.

The substance quantity amounts are varied in the same way as with the catalyst components, i.e., by crossing and mutation, and to this extent reference is also made to International Patent 00/15341.

The preferred number of generations is between 5 and 50.

The preferred number of individual components in the first generation is between 10 und 30.

The preferred number of individual components in a mixed material of the first generation is between 3 and 10.

It has also been found that in determining the performance parameters of the newly structured material compositions of the next generations, it is advantageous to vary the composition of the gas stream, the space velocity of the gas based on the catalyst mass and/or the temperature.

It is especially advantageous if, in determination of the performance parameters of the newly structured material compositions of the next generations, the composition of the gas stream, the space velocity of the gas based on the catalyst mass and the temperature are varied according to the principles of mutation and crossing.

As explained above, the evolutionary strategies such as crossing and mutation (implemented in actual practice by using numerical random generators with a uniform distribution B in contrast with random generators with a logarithmic normal distribution, a Weibull distribution, a Candy distribution, etc.) are implemented in this way, despite the fact that extraction and cubing are also equivalent stochastic methods. In the case of numerical random generators, the program codes G05CAF, G05DYF, G05DZF or G05CCF of the NAG LIBRARY (NAG FORTRAN WORKSTATION LIBRARY, NAG Group Ltd., 1986) of a numerical random generator are used to advantage.

Random generators which are freely available on the Internet or those available commercially as software such as "Numerical Recipes in FORTRAN, PASCAL or C" from the Cambridge University Press, or IMSL libraries of the FORTRAN compilers DIGITAL Visual Fortran Professional Edition may also be used.

Thus, for example, by using such methods, several catalyst components can be selected and their corresponding molar substance amounts exchanged among the previously selected catalysts components (crossing). In this way, it is also possible to bring about an exchange of the individual catalyst components themselves by means of crossing for the use of quantitative amounts which are altered from a finite value to zero or from zero to a finite value, thus obtaining on the whole a new composition of a catalyst of the new generation. However, a catalyst component selected by random generator, for example, can also be increased or reduced (mutation) by multiplying by factors that are either freely selected or are randomly determined from the quantity of real numbers between 0 and 10,000, so that although the new catalyst of the next catalyst generation contains the same components, they are present in a different concentration and thus also the ratios of the components to one another can be altered.

BRIEF DESCRIPTION OF THE DRAWINGS

This invention is explained in greater detail below on the basis of an example. The respective drawings show:

FIG. 2: Schematic diagram of crossing and mutation.

DETAILED DESCRIPTION OF THE INVENTION

Figure 1:
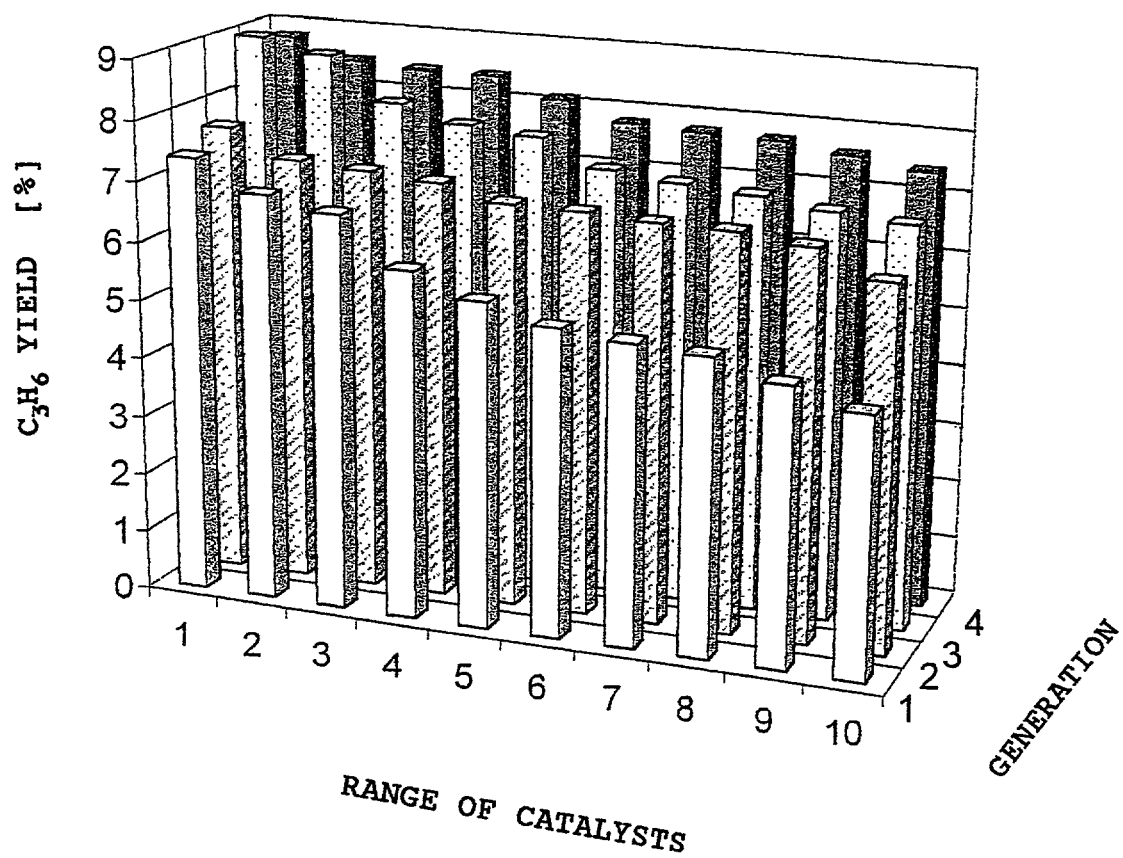
FIG. 1: A bar chart showing propylene yields of the ten best catalysts of a generation as a function of their increase within four generations.

With reference to FIG. 2, it should be pointed out that the primary components listed on the left in each case are the elements used in producing the catalytic materials, where the index 1 denotes that this component is present in the catalyst, while the index 0 describes the absence of this component.

EXAMPLE

Catalysts were prepared and tested with the goal of converting propane to propylene by oxidation with oxygen and minimizing the resulting CO and $CO_2$ oxides. The course of this process included the following steps and led to the results described below.

Experimental procedure

The starting components containing the primary components of the mixed catalysts were first dissolved or suspended in water and mixed with "$\alpha$-$Al_2O_3$ (CONDEA, particle diameter =1.0 mm, $S_{BET}$=5 m$^2$/g), which functioned as an inert diluent material. The volume of the solution/dispersion used per 1 g $Al_2O_3$ was 10 mL. The mixture was stirred for 30 minutes at 80° C. Excess water was evaporated off while stirring at 100° C. The remaining solid was dried at 120° C. for ten hours and calcined in air for three hours at 600° C. The starting compounds were: $NH_4VO_3$ (Merck, analytical purity), $Mg(NO_3)_2 \cdot 4H_2O$ (Merck, analytical purity), $H_3BO_3$ (Merck, analytical purity), $(NH_4)_6Mo_7O_{24} \cdot 4H_2O$ (Riedel de Haën, analytical purity), $La(NO_3)_2 \cdot 6H_2O$ (Merck, analytical purity), $Mn(NO_3)_2 \cdot 4H_2O$ (Merck, p. a.), $Fe(NO_3)_3 \cdot 9H_2O$ (Fluka, analytical purity), $Ga(NO_3)_2 \cdot 6H_2O$ (Alfa, 99.9%).

The performance parameters of the catalysts were determined in U-shaped tubular reactors (I.D. =6 mm) made of quartz and operated in parallel. To minimize the temperature reaction temperature was 500° C. in all the experiments. The reaction gas mixture consisted of propane, oxygen and nitrogen ($C_3H_8/O_2/N_2$=3/1/6); 0.3 g catalyst was used. The total volume flow was varied in the range of 10 to 150 mL/min (STP). On-line gas chromatography was used for analysis of the reaction gases.

Results

First step:

Production of the first generation of catalytic materials from the primary components identified.

The compositions of different catalytic materials were determined according to the random principle (see Table 1) by combining four primary components per material. The total number of materials of the first generation was 56. This number was retained in all further generations. Table 1 summarizes the compositions of the first generation catalysts.

Second step:

Parallel preparation and testing of first generation catalytic materials.

The materials were produced according to the procedure described in the experimental section and were tested in parallel. The propylene yields obtained with the first-generation catalysts are shown in FIG. 1.

Third step

Producing the second generation based on the results of testing the first generation of catalysts.

First, 37 mixed catalysts of the second generation were produced by crossing. To do so, two mixed oxide catalysts were selected from the first generation, one of the two catalysts (catalyst A) being selected randomly while the other catalyst (catalyst B) was selected with the probability $W_i$ which is determined by the catalytic performance parameters according to the formulation:

$$W_i = \frac{\left(\sum_{j=1}^{n} j\right) - i}{\left(\sum_{j=1}^{n} j\right)}$$

where i and j denote the ranking of the catalysts of a generation, arranged in order of decreasing catalytic activity (shown in Table 3, column 1 for the 10 strongest catalysts) and n denotes the total number of catalysts of a generation, which in this example amounts to 56. Then a primary component present in only one of the two catalysts was selected from the two mixed catalysts A and B according to the random principle. This component was added to the catalyst which did not originally contain this component, and it was removed from the catalyst which did originally contain this component. In the case of the crossing illustrated in FIG. 2, this concerns the primary component boron.

In addition, 19 catalysts of the second catalyst generation were produced by mutation. To do so, a mixed catalyst was selected arbitrarily from a catalyst generation, and a primary component contained in the catalyst was removed according to the random principle, and the component which was not previously present in this catalyst was added. In the case of mutation illustrated in FIG. 2, this pertains to the primary component manganese.

Subsequent steps:

Repeating the second and third steps for the coming generations.

By repeating steps 2 and 3, a total of four catalyst generations were tested, including testing of a total of 224 catalytic material materials. The propylene yields of the ten best catalysts of a generation are shown in FIG. 1. The compositions of the catalytic materials of the fourth generation are documented in Table 2.

Most mixed catalysts which give good yields consist of V, Mg, Mo, Ga or V, Mg, Ga. FIG. 1 shows that a reproducible increase in propylene yield of the most efficient catalyst of a generation is achieved from one generation to the next. The following compositions led to the best $C_3H_6$ yields: $V_{0.25}Mg_{0.52}Mo_{0.12}Ga_{0.11}O_x$. (first generation), $V_{0.47}Mo_{0.05}Mn_{0.27}Ga_{0.21}O_x$. (second generation), $V_{0.27}Mg_{0.47}Mo_{0.11}Ga_{0.20}O_x$. (third generation), $V_{0.27}Mg_{0.37}Mo_{0.12}Fe_{0.13}Ga_{0.11}O_x$. (fourth generation). The highest $C_3H_6$ yield was 9.0% (selectivity 57.4%).

In the compositions of the fourth generation, it is clear that even after the fourth generation, all the primary components are still represented in the generation, although the presence of components which did not lead to any significant propylene yield in the first generations is low. This is attributable to the selection principles for restructuring of the catalyst according to the present invention, said principles ensuring a higher target accuracy of the optimization process than achieved with a purely performance-oriented catalyst selection. Thus, in comparison with methods known in the art, a higher catalyst performance is achieved in optimization with the procedure described above.

TABLE 1

Composition of catalytic materials of the first generation

| Cat. No. | V | Mg | B | Mo | La | Mn | Fe | Ga |
|---|---|---|---|---|---|---|---|---|
| 1 | 0.24 | | | | 0.33 | | 0.15 | 0.28 |
| 2 | | 0.42 | | 0.11 | | 0.20 | 0.28 | |
| 3 | | | 0.41 | 0.31 | | | 0.05 | 0.24 |
| 4 | 0.47 | | | 0.14 | 0.27 | | | 0.12 |
| 5 | | | 0.42 | 0.29 | | 0.23 | | 0.06 |
| 6 | | 0.36 | 0.10 | | | 0.41 | 0.13 | |
| 7 | | | | 0.32 | 0.20 | 0.26 | 0.22 | |
| 8 | | 0.21 | | 0.15 | | | 0.33 | 0.32 |
| 9 | 0.16 | | | | 0.27 | 0.10 | | 0.46 |
| 10 | | 0.30 | 0.28 | 0.13 | | | 0.28 | |
| 11 | | | 0.27 | | | 0.45 | 0.06 | 0.22 |
| 12 | | | | 0.17 | 0.14 | 0.56 | 0.13 | |
| 13 | | 0.34 | | | 0.19 | 0.16 | | 0.30 |
| 14 | | 0.36 | 0.08 | | 0.25 | | 0.32 | |
| 15 | 0.44 | | | 0.11 | | 0.26 | | 0.19 |
| 16 | 0.05 | 0.30 | | | 0.41 | | | 0.24 |
| 17 | 0.10 | 0.05 | 0.44 | | | 0.41 | | |
| 18 | 0.42 | 0.40 | | | | | 0.04 | 0.14 |
| 19 | | 0.02 | | | 0.51 | 0.25 | 0.22 | |
| 20 | 0.25 | 0.52 | | 0.12 | | | | 0.11 |
| 21 | | 0.33 | | 0.31 | 0.20 | | 0.15 | |
| 22 | 0.002 | | 0.37 | | | | 0.18 | 0.45 |
| 23 | 0.08 | | | 0.49 | 0.40 | | 0.04 | |
| 24 | | 0.13 | | 0.43 | 0.14 | | | 0.29 |
| 25 | | 0.39 | | | 0.46 | | 0.04 | 0.12 |
| 26 | | 0.05 | | 0.19 | | 0.53 | 0.22 | |
| 27 | | 0.29 | | 0.24 | 0.33 | | | 0.13 |
| 28 | 0.04 | | 0.46 | 0.25 | 0.26 | | | |
| 29 | 0.05 | | | | 0.26 | 0.29 | | 0.3 |
| 30 | | 0.32 | | | | 0.09 | 0.42 | 0.18 |
| 31 | 0.005 | | | 0.42 | | | 0.17 | 0.41 |
| 32 | | 0.42 | 0.09 | | | 0.02 | | 0.47 |
| 33 | 0.27 | 0.35 | | 0.05 | 0.34 | | | |
| 34 | 0.47 | | 0.15 | | | | 0.35 | 0.03 |
| 35 | | 0.31 | | 0.24 | 0.14 | | 0.31 | |
| 36 | 0.22 | | 0.38 | 0.13 | | 0.27 | | |
| 37 | | | 0.05 | 0.32 | 0.02 | | 0.61 | |
| 38 | 0.24 | | | | | 0.26 | | 0.27 |
| 39 | | 0.05 | | 0.45 | | 0.12 | 0.39 | |
| 40 | 0.26 | | | | 0.07 | | 0.59 | 0.08 |
| 41 | | 0.11 | 0.12 | | 0.09 | | | 0.68 |
| 42 | 0.28 | | | 0.23 | 0.3 | 0.19 | | |
| 43 | 0.05 | | 0.24 | 0.38 | | | | 0.32 |
| 44 | | 0.41 | | | 0.24 | | 0.24 | 0.12 |
| 45 | | 0.2 | | 0.24 | | 0.34 | | 0.21 |
| 46 | 0.44 | | 0.28 | | 0.03 | | | 0.24 |
| 47 | 0.25 | 0.35 | | 0.27 | | | 0.13 | |
| 48 | 0.36 | | | | | 0.3 | 0.25 | 0.09 |
| 49 | | 0.7 | 0.1 | | | 0.12 | | 0.08 |
| 50 | | | 0.22 | | 0.13 | 0.32 | | 0.33 |
| 51 | 0.27 | 0.34 | | 0.21 | | | 0.18 | |
| 52 | 0.13 | | | | | 0.07 | 0.43 | 0.37 |
| 53 | | | | 0.23 | 0.21 | 0.24 | 0.31 | |
| 54 | 0.18 | 0.2 | | | | | 0.32 | 0.3 |
| 55 | | | 0.31 | | | 0.28 | | 0.17 |
| 56 | | 0.26 | | | | 0.34 | 0.004 | 0.39 |

TABLE 2

Composition of catalytic materials of the fourth generation

| Cat. No. | V | Mg | B | Mo | La | Mn | Fe | Ga |
|---|---|---|---|---|---|---|---|---|
| 1 | 0.30 | | | 0.34 | | 0.36 | | |
| 2 | 0.36 | 0.22 | | 0.18 | | 0.09 | | 0.15 |
| 3 | 0.20 | 0.28 | | 0.09 | | | 0.10 | 0.32 |
| 4 | 0.21 | 0.53 | | 0.16 | | 0.10 | | |
| 5 | 0.22 | 0.47 | | 0.21 | | | | 0.10 |

TABLE 2-continued

Composition of catalytic materials of the fourth generation

| Cat. No. | V | Mg | B | Mo | La | Mn | Fe | Ga |
|---|---|---|---|---|---|---|---|---|
| 6 | 0.27 | 0.55 | | 0.09 | | | | 0.12 |
| 7 | 0.71 | | | 0.09 | | 0.20 | | |
| 8 | 0.27 | 0.37 | | 0.12 | | | 0.13 | 0.11 |
| 9 | 0.20 | 0.28 | | 0.09 | | 0.26 | 0.10 | 0.06 |
| 10 | 0.54 | | | 0.14 | | 0.32 | | |
| 11 | 0.29 | 0.28 | | | 0.31 | | 0.03 | 0.10 |
| 12 | 0.18 | 0.25 | | 0.08 | | | 0.09 | 0.40 |
| 13 | 0.44 | | | 0.25 | | 0.13 | | 0.20 |
| 14 | 0.18 | 0.26 | | 0.19 | | | 0.10 | 0.27 |
| 15 | 0.51 | | | 0.13 | | 0.15 | | 0.21 |
| 16 | 0.52 | | | 0.24 | | | | 0.23 |
| 17 | | 0.51 | | 0.20 | | 0.29 | | |
| 18 | 0.44 | | 0.17 | | | 0.29 | 0.04 | 0.06 |
| 19 | 0.28 | | | 0.07 | | 0.07 | 0.46 | 0.12 |
| 20 | 0.13 | 0.19 | | 0.14 | | | 0.14 | 0.39 |
| 21 | 0.16 | 0.21 | | | | | 0.11 | 0.52 |
| 22 | | | 0.34 | | | 0.55 | | 0.11 |
| 23 | 0.40 | | | 0.20 | | 0.23 | | 0.17 |
| 24 | 0.21 | 0.26 | | 0.07 | | | 0.14 | 0.33 |
| 25 | 0.23 | 0.22 | | 0.45 | | | 0.02 | 0.08 |
| 26 | 0.41 | 0.25 | | 0.10 | | 0.05 | | 0.18 |
| 27 | 0.19 | 0.39 | | 0.09 | | | | 0.33 |
| 28 | 0.40 | | | 0.05 | | 0.23 | | 0.33 |
| 29 | 0.18 | 0.78 | | | | | | 0.04 |
| 30 | 0.42 | 0.44 | | 0.10 | | | | 0.05 |
| 31 | | 0.77 | | 0.23 | | | | |
| 32 | 0.47 | | | 0.06 | | 0.27 | | 0.20 |
| 33 | 0.64 | 0.30 | | | | | 0.06 | |
| 34 | 0.27 | 0.34 | | 0.09 | | | 0.19 | 0.11 |
| 35 | 0.54 | | | 0.14 | | 0.32 | | |
| 36 | 0.50 | | | | | 0.29 | | 0.21 |
| 37 | 0.45 | 0.14 | | 0.11 | | 0.11 | | 0.19 |
| 38 | 0.19 | 0.48 | | 0.15 | | | 0.12 | 0.06 |
| 39 | | 0.40 | | 0.16 | | 0.16 | | 0.28 |
| 40 | 0.20 | 0.43 | | 0.10 | | | 0.22 | 0.05 |
| 41 | 0.29 | 0.38 | | 0.23 | | | | 0.10 |
| 42 | | | | | 0.15 | | | 0.85 |
| 43 | 0.29 | 0.31 | | 0.14 | | | | 0.26 |
| 44 | 0.18 | 0.37 | | 0.08 | | | 0.33 | 0.04 |
| 45 | 0.47 | | | 0.05 | | 0.28 | | 0.20 |
| 46 | 0.28 | 0.59 | | 0.07 | | | | 0.06 |
| 47 | 0.16 | 0.20 | | 0.12 | 0.36 | | 0.11 | 0.05 |
| 48 | 0.30 | 0.39 | | 0.24 | | | | 0.07 |
| 49 | 0.20 | | | 0.15 | | 0.65 | | |
| 50 | 0.46 | 0.49 | | | | | | 0.05 |
| 51 | 0.13 | 0.67 | | 0.20 | | | | |
| 52 | 0.09 | 0.21 | 0.39 | | | | | 0.32 |
| 53 | 0.41 | 0.25 | | 0.10 | | 0.05 | | 0.18 |
| 54 | 0.34 | 0.48 | | | | | 0.17 | |
| 55 | 0.14 | 0.20 | | 0.15 | | 0.20 | 0.08 | 0.42 |
| 56 | 0.28 | 0.57 | | 0.13 | | | | |

TABLE 3

Composition of the ten best catalytic materials yielding the highest propylene yield in each generation

| i or j | Generation 1 | Generation 2 | Generation 3 | Generation 4 |
|---|---|---|---|---|
| 1 | $V_{0.25}Mg_{0.52}Mo_{0.12}Ga_{0.11}O_x$ | $V_{0.47}Mo_{0.05}Mn_{0.27}Ga_{0.2}O_x$ | $V_{0.22}Mg_{0.47}Mo_{0.11}Ga_{0.2}O_x$ | $V_{0.27}Mg_{0.37}Mo_{0.12}Fe_{0.13}Ga_{0.1}O_x$ |
| 2 | $V_{0.44}Mo_{0.11}Mn_{0.26}Ga_{0.19}O_x$ | $V_{0.35}Mg_{0.33}Fe_{0.03}Ga_{0.28}O_x$ | $V_{0.3}Mg_{0.63}Ga_{0.07}O_x$ | $V_{0.29}Mg_{0.31}Mo_{0.14}Ga_{0.26}O_x$ |
| 3 | $V_{0.42}Mg_{0.4}Fe_{0.04}Ga_{0.14}O_x$ | $V_{0.39}Mo_{0.22}Mn_{0.23}Ga_{0.17}O_x$ | $V_{0.14}Mg_{0.2}Mo_{0.15}Fe_{0.08}Ga_{0.42}O_x$ | $V_{0.19}Mg_{0.39}Mo_{0.09}Ga_{0.33}O_x$ |
| 4 | $V_{0.27}Mg_{0.34}Mo_{0.21}Fe_{0.18}O_x$ | $Mg_{0.26}Mo_{0.31}Mn_{0.44}O_x$ | $V_{0.4}Mg_{0.42}Mo_{0.09}Ga_{0.09}Ox$ | $V_{0.35}Mg_{0.3}Mo_{0.2}Mn_{0.15}Ga_{0.08}O_x$ |
| 5 | $V_{0.36}Mn_{0.3}Fe_{0.25}Ga_{0.09}O_x$ | $V_{0.27}Mo_{0.19}Fe_{0.43}Ga_{0.11}O_x$ | $V_{0.39}Mg_{0.24}Mo_{0.1}Mn_{0.1}Ga_{0.17}O_x$ | $V_{0.41}Mg_{0.25}Mo_{0.1}Mn_{0.05}Ga_{0.18}O_x$ |
| 6 | $V_{0.18}Mg_{0.2}Fe_{0.32}Ga_{0.3}O_x$ | $V_{0.31}Mg_{0.39}Mo_{0.1}Fe_{0.21}O_x$ | $V_{0.24}Mg_{0.32}Mo_{0.19}Fe_{0.16}Ga_{0.08}O_x$ | $V_{0.42}Mg_{0.44}Mo_{0.1}Ga_{0.05}O_x$ |
| 7 | $V_{0.25}Mg_{0.35}Mo_{0.27}Fe_{0.13}O_x$ | $V_{0.3}Mg_{0.42}Mo_{0.13}Fe_{0.17}O_x$ | $V_{0.27}Mg_{0.38}Mo_{0.12}Fe_{0.14}Ga_{0.08}O_x$ | $V_{0.27}Mg_{0.34}Mo_{0.09}Fe_{0.19}Ga_{0.11}O_x$ |
| 8 | $B_{0.42}Mo_{0.09}Mn_{0.02}Ga_{0.47}O_x$ | $V_{0.24}La_{0.12}Ga_{0.65}O_x$ | $V_{0.53}Mg_{0.25}Fe_{0.05}Ga_{0.18}O_x$ | $V_{0.2}Mg_{0.28}Mo_{0.09}Fe_{0.1}Ga_{0.32}O_x$ |
| 9 | $V_{0.26}La_{0.07}Mo_{0.59}Ga_{0.08}O_x$ | $V_{0.52}Mo_{0.13}Mn_{0.13}Ga_{0.22}O_x$ | $V_{0.55}Mo_{0.06}Mn_{0.16}Ga_{0.23}O_x$ | $V_{0.47}Mg_{0.05}Mn_{0.28}Ga_{0.2}O_x$ |
| 10 | $V_{0.47}B_{0.15}Fe_{0.35}Ga_{0.03}O_x$ | $V_{0.27}Mg_{0.57}Mo_{0.13}Ga_{0.06}O_x$ | $V_{0.23}Mg_{0.59}Mo_{0.18}O_x$ | $V_{0.18}Mg_{0.26}Mo_{0.19}Fe_{0.1}Ga_{0.27}O_x$ |

The invention claimed is:

1. A method for producing an improved catalyst, said method comprising:
   (a) providing a first catalyst generation comprising a plurality of mixed catalysts, each said mixed catalyst comprising a plurality of components;
   (b) measuring at least one performance parameter for each catalyst of said first catalyst generation;
   (c) preparing a second catalyst generation by restructuring the catalysts of said first generation by a pre-determined number of processes comprising crossing or mutation or both, performed in any order;
   (d) repeating steps (a) through (c) for a predetermined number of generations or until no definite improvement in catalytic properties is observed within a generation, wherein each second catalyst generation provides the first catalyst generation of a subsequent generation,
   wherein said crossing process comprises the steps of:
   (i) ranking said first catalyst generation according to said at least one performance parameter;
   (ii) selecting a first mixed catalyst using a numerical random generator having a uniform distribution;
   (iii) selecting a second mixed catalyst with a probability Wi using a numerical random generator having a uniform distribution, wherein Wi is determined according to the formula:

$$W_i = \frac{\left(\sum_{j=1}^{n} j\right) - i}{\left(\sum_{j=1}^{n} j\right)}$$

wherein i and j denote said ranking in order of decreasing performance, and n denotes the number of catalysts in said first catalyst generation;
   (iv) selecting from said first and second mixed catalysts a first component that is present in only one of said first and second mixed catalysts using a numerical random generator having a uniform distribution; and
   (v) crossing said first and second catalyst by removing said first component from said first or second catalyst having said first component, and adding said first component to said first or second catalyst lacking said first component;
   and wherein said mutation process comprises the steps of:
   (vi) selecting a third mixed catalyst using a numerical random generator having a uniform distribution;

(vii) selecting a component of said third mixed catalyst using a numerical random generator having a uniform distribution; and (viii) mutating said third mixed catalyst by adding said component if said third mixed catalyst lacks said component, or removing said component if said third mixed catalyst has said first component.

2. The method of claim 1, wherein said pre-determined number of generations is between about 5 and about 50.

3. The method of claim 1, wherein the number of said components in the mixed catalysts of said first catalyst generation is between about 3 and about 30.

4. The method of claim 3, wherein the number of said components in the mixed catalysts of said first catalyst generation is between about 3 and about 10.

5. The method of claim 1, wherein said at least one performance parameter of said catalyst is determined by contacting said catalyst with a gas stream, wherein the composition of the gas stream is varied.

6. The method of claim 1, wherein the gas stream has a space velocity, and wherein the space velocity of the gas is varied based on the catalyst mass in determining said performance parameters of said catalysts.

7. The method of claim 1, wherein the temperature of said catalyst is varied in the determination of said performance parameters of said catalysts.

8. The method of claim 5, wherein the composition of the catalyst, the space velocity of the gas based on the catalyst mass, and the temperature, are varied according to the principles of mutation and crossing to determine the performance parameters of the newly structured material compositions of the next generations.

* * * * *